(12) United States Patent
Feng

(10) Patent No.: US 10,769,922 B2
(45) Date of Patent: Sep. 8, 2020

(54) HELP SEEKING METHOD, SYSTEM, AND APPARATUS, AND COMPUTER STORAGE MEDIUM

(71) Applicant: Tencent Technology (Shenzhen) Company Limited, Shenzhen, Guangdong (CN)

(72) Inventor: Wang Da Feng, Guangdong (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 0 days.

(21) Appl. No.: 15/950,425

(22) Filed: Apr. 11, 2018

(65) Prior Publication Data
US 2018/0233015 A1 Aug. 16, 2018

Related U.S. Application Data

(63) Continuation of application No. PCT/CN2017/078196, filed on Mar. 24, 2017.

(30) Foreign Application Priority Data

Mar. 24, 2016 (CN) .................... 2016 1 01733687

(51) Int. Cl.
*B60Q 1/00* (2006.01)
*G08B 21/02* (2006.01)
(Continued)

(52) U.S. Cl.
CPC .......... *G08B 21/02* (2013.01); *B60R 21/0136* (2013.01); *G01S 19/42* (2013.01);
(Continued)

(58) Field of Classification Search
CPC ......... B60R 2021/0027; B60R 21/0136; G01S 19/42; G06Q 50/00; G06Q 50/01;
(Continued)

(56) References Cited

U.S. PATENT DOCUMENTS 5,327,990 A 7/1994 Busquets
2007/0244633 A1 10/2007 Phillips et al.
(Continued)

FOREIGN PATENT DOCUMENTS

CN 101404705 A 4/2009
CN 101499208 A 8/2009
(Continued)

OTHER PUBLICATIONS

Office Action dated Dec. 3, 2018 for Chinese Application No. 201610173368.7, 20 pages.
(Continued)

*Primary Examiner* — Naomi J Small
(74) *Attorney, Agent, or Firm* — Brinks Gilson & Lione

(57) ABSTRACT

Disclosed are help seeking methods, systems, and apparatuses, and computer storage mediums storing processor executable instructions for implementing the help seeking methods. A help seeking system includes a distress device, a distress device server, a social server, and a social client. A distress device in a vehicle obtains a geographical location and a device identifier of the distress device, and sends a rescue request to the social server. The social server receives the rescue request, determines a social client associated with the device identifier, sends the rescue request to the social client, and sends the rescue request to the distress device server. The social client and the distress device server separately receives the rescue request sent by the social server. Therefore, a rescue efficiency can be improved in scenarios where a driver is not able to request assistance.

14 Claims, 14 Drawing Sheets

(51) Int. Cl.
  G08B 25/00 (2006.01)
  G06Q 50/00 (2012.01)
  G16H 40/20 (2018.01)
  B60R 21/0136 (2006.01)
  G01S 19/42 (2010.01)
  H04L 12/58 (2006.01)
  B60R 21/00 (2006.01)

(52) U.S. Cl.
  CPC ............ *G06Q 50/00* (2013.01); *G06Q 50/01* (2013.01); *G08B 25/00* (2013.01); *G16H 40/20* (2018.01); *H04L 51/32* (2013.01); *B60R 2021/0027* (2013.01)

(58) Field of Classification Search
  CPC ........ G08B 21/02; G08B 25/00; G16H 40/20; H04L 51/32
  USPC .......................................................... 340/436
  See application file for complete search history.

(56) References Cited

U.S. PATENT DOCUMENTS

| | | | |
|---|---|---|---|
| 2010/0248681 A1* | 9/2010 | Phills | H04L 67/04 455/404.2 |
| 2014/0046701 A1 | 2/2014 | Steinberg et al. | |
| 2014/0300739 A1* | 10/2014 | Mimar | G08B 21/06 348/148 |
| 2014/0368601 A1* | 12/2014 | deCharms | H04L 65/403 348/14.02 |
| 2015/0065082 A1* | 3/2015 | Sehgal | G08B 25/016 455/404.2 |
| 2016/0029197 A1* | 1/2016 | Gellens | H04Q 9/00 455/404.1 |
| 2016/0071333 A1* | 3/2016 | Haidar | G07C 5/0808 701/29.3 |
| 2016/0087655 A1* | 3/2016 | Kim | H04W 4/029 455/404.1 |
| 2016/0315902 A1* | 10/2016 | Silva | H04W 4/21 |
| 2017/0374538 A1* | 12/2017 | Gellens | H04W 4/90 |

FOREIGN PATENT DOCUMENTS

| | | |
|---|---|---|
| CN | 101556735 A | 10/2009 |
| CN | 101807337 A | 8/2010 |
| CN | 102039865 A | 5/2011 |
| CN | 102868735 A | 1/2013 |
| CN | 202863368 U | 4/2013 |
| CN | 103247169 A | 8/2013 |
| CN | 203406964 U | 1/2014 |
| CN | 103569008 A | 2/2014 |
| CN | 103903406 A | 7/2014 |
| CN | 104554106 A | 4/2015 |
| CN | 204314957 U | 5/2015 |
| CN | 105262792 A | 1/2016 |
| CN | 105407456 A | 3/2016 |
| CN | 105761425 A | 7/2016 |
| DE | 3830301 A1 | 3/1990 |
| JP | 2004-171394 A | 6/2004 |
| JP | 3672838 B2 | 7/2005 |
| JP | 2015-176566 A | 10/2015 |
| KR | 10-1999-0061410 A | 7/1999 |
| KR | 10-2008-0065047 A | 7/2008 |
| KR | 10-2010-0073893 A | 7/2010 |
| KR | 10-2012-0087058 A | 8/2012 |
| KR | 10-1589214 B1 | 1/2016 |
| WO | WO 2014/047695 A2 | 4/2014 |
| WO | WO 2014/047695 A3 | 4/2014 |
| WO | WO 2014/047695 A8 | 4/2014 |

OTHER PUBLICATIONS

ISR and Written Opinion corresponding to PCT Application No. PCT/CN2017/078196, dated Jun. 29, 2017, 13 pages.
Office Action dated Apr. 23, 2019 for Chinese Application No. 201610173368.7, 19 pages.
Masaya Kaneda, et al., "A Study on Acquisition Methods of Position Information in the Biomedical Information Monitoring System", Multimedia, Distributed, Cooperative and Mobile (DICOMO) Symposium Proceedings, 1997-2006 edition, Japan, Information Processing Society of Japan, Jun. 27, 2001, vol. 7, 9 pages.
Office Action dated Jul. 8, 2019 for Japanese Application No. 2018-521067, 5 pages.
Office Action dated May 10, 2019 for Korean Application No. 10-2018-7011377, 10 pages.
Meyer, Gereon et al., "Advanced Microsystems for Automotive Applications 2010: Smart Systems for Green Cars and Safe Mobility," Apr. 5, 2011, Springer 2010, ISBN: 978-3-642-12647-5, pp. ToC, Pref, 3-12, 61-68, 177-188, 279-288, 347-363, 443-452 and AppB, (84 pages).
Coulouris, George et al., "Distributed Systems: Concepts and Design (Fifth Edition)", May 7, 2011, Addison-Wesley, ISBN: 978-0-13-214301-1; pp. ToC, Pre, Chapters 1-4, 6-7, 9, 11, 19 and 21, References and Index, (598 pages).
Tarkoma, Sasu et al., "Publish/Subscribe Systems: Design and Principles (First Edition)," Aug. 3, 2012, Wiley, ISBN: 978-1-119-95154-4, pp. ToC, Chapters 1-2, 4, 6-7,12, 14 and Index, (173 pages).
Schulzrinne, Henning et al., "Internet Protocol-based Emergency Services," Jul. 12, 2013, Wiley, ISBN: 978-0-470-68976-9, pp. ToC and 240-394, (163 pages).
Adibi, Sasan, "Mobile Health: A Technology Road Map," Feb. 19, 2015, Springer International Publishing, ISSN: 2193-9349 ISBN: 978-3-319-12816-0, vol. 5, pp. ToC and Chapter 13, (23 pages).
Wikipedia, "Mobile Web," Internet article dated Feb. 8, 2016, Retrieved from the Internet at <http://en.wikipedia.org/w/index.php?title=Mobile_web&oldid=703856006> on Dec. 6, 2019, 7 pages.
Wikipedia, "Vehicle tracking system," Internet article dated Feb. 29, 2016, Retrieved from the Internet at <http://en.wikipedia.org/w/index.php?title=Vehicle_tracking_system&oldid=707595937> on Jul. 26, 2018, 5 pages.
Wikipedia, "TomTom," Internet article dated Mar. 15, 2016, Retrieved from the Internet at <http://en.wikipedia.org/w/index.php?title=TomTom&oldid=710168923> on Dec. 6, 2019, 11 pages.
Wikipedia, "eCall," Internet article dated Mar. 22, 2016, Retrieved from the Internet at <http://de.wikipedia.org/w/index.php?title=ECall&oldid=152755554> on Jul. 26, 2018, 6 pages.
Examination Report dated Jan. 2, 2020 for European Application No. 17769489.0, 2 pages.

* cited by examiner

HELP SEEKING METHOD, SYSTEM, AND APPARATUS, AND COMPUTER STORAGE MEDIUM

CROSS-REFERENCE TO RELATED APPLICATION(S)

This application is a continuation of International Patent Application No. PCT/CN2017/078196, filed on Mar. 24, 2017, which claims priority to Chinese Patent Application No. 2016101733687, filed with the State Intellectual Property Office of the People's Republic of China on Mar. 24, 2016, the entirety of all of which are hereby incorporated by reference herein.

FIELD OF THE TECHNOLOGY

This application relates to the field of intelligent transportation, and in particular, to a help seeking method, system, and apparatus, and a computer storage medium.

BACKGROUND OF THE DISCLOSURE

With continued positive economic developments, more people choose riding in private cars as a transportation solution instead of walking. It follows that a quantity of vehicles on the road increases, and mathematically the probability of a traffic accident occurring increases as well.

When a vehicle is involved in an accident, usually, an owner of the vehicle in the accident seeks help from emergency workers, relatives, or friends by himself or herself. Sometimes, a helpful passerby may contact a rescue worker on behalf of the vehicle owner. In some cases, no one may contact the rescue worker until traffic police arrive at the scene of the accident.

Under these scenarios, the following problem exists: An owner of a vehicle in an accident may actively seek help only when the owner's ability to perform such actions are not affected. However, when the owner is seriously injured or not conscious (e.g., in a coma), and other rescue workers cannot arrive in time, the early response time for rescuing the owner of the vehicle in the accident may be easily missed.

SUMMARY

To resolve the problem in the existing technology, this application provides a help seeking method, system, and apparatus, and a computer storage medium. The technical solutions are as described herein.

A first embodiment provides a help seeking method applied to a help seeking system, where the help seeking system includes a distress device, a distress device server, a social server separately connected to the distress device and the distress device server, and a social client. According to some embodiments the social server may be a background server of the social client. The help seeking method may include obtaining, by a distress device in the vehicle, a geographical location and a device identifier of the distress device. The help seeking method may further include sending, by the distress device, a rescue request to the social server, where the rescue request includes at least the geographical location and the device identifier. The help seeking method may further include receiving the rescue request sent by the distress device, determining a social client associated with the device identifier, and sending the rescue request to the social client. The help seeking method may further include receiving, by the social client, the rescue request sent by the social server, and sending, by the social server, the rescue request to the distress device server. The help seeking method may further include the distress device server: receiving the rescue request sent by the social server, and instructing a rescue worker to head for the geographical location to carry out rescue.

A second embodiment provides a help seeking method applied to a distress device server connected to a social server. The help seeking method may include receiving a rescue request from the social server, where the rescue request is sent to the social server by a distress device in a vehicle when the vehicle is in a collision. The rescue request may include at least a geographical location of the vehicle and a device identifier of the distress device. The help seeking method may further include instructing a rescue worker to travel to the geographical location of the vehicle identified in the rescue request to carry out rescue.

A third embodiment provides a help seeking method applied to a social server. The help seeking method may include receiving a rescue request sent by a distress device in a vehicle when the vehicle is in a collision. The rescue request may include at least a geographical location of the vehicle and a device identifier. The help seeking method may further include determining a social client associated with the device identifier, sending the rescue request to the social client, and sending the rescue request to a distress device server.

A fourth embodiment provides a help seeking system including a distress device, a distress device server, a social server separately connected to the distress device and the distress device server, and a social client. According to some embodiments the social server may be a background server of the social client. The help seeking system may include a distress device installed in the vehicle that obtains a geographical location and a device identifier of the distress device when the vehicle is in an accident. The distress device may further send a rescue request to the social server, where the rescue request includes at least the geographical location and the device identifier. The social server may receive the rescue request sent by the distress device, determine a social client associated with the device identifier, and send the rescue request to the social client. The social client may receive the rescue request sent by the social server. The social server may further send the rescue request to the distress device server. The distress device server may receive the rescue request sent by the social server, and instruct a rescue worker to travel to the geographical location identified in the rescue request to carry out rescue.

A fifth embodiment provides a help seeking apparatus including a distress device server connected to a social server. The help seeking apparatus may receive a rescue request sent by the social server, where the rescue request is sent to the social server by a distress device in a vehicle when the vehicle is in a collision. The rescue request may include at least a geographical location of the vehicle and a device identifier of the distress device. The help seeking apparatus may further instruct a rescue worker to travel to the geographical location of the vehicle identified in the rescue request to carry out rescue.

A sixth embodiment provides a help seeking apparatus including a social server. The help seeking apparatus may receive a rescue request sent by a distress device in a vehicle when the vehicle has a collision, the rescue request including at least a geographical location of the vehicle and a device identifier. The help seeking apparatus may further determine a social client associated with the device identifier, and send the rescue request to the social client. The help seeking apparatus may further send the rescue request to a distress device server.

A seventh embodiment provides a computer storage medium storing processor-executable instructions that, when executed by a processor, cause the processor to obtain a geographical location and a device identifier of a distress device when a vehicle is in a collision. The instructions may further cause the processor to control a distress device to send a rescue request to a social server, where the rescue request includes at least the geographical location and the device identifier. The instructions may further cause the processor to control the social server to receive the rescue request sent by the distress device, determine a social client associated with the device identifier, and send the rescue request to the social client. The instructions may further cause the processor to control the social client to receive the rescue request sent by the social server. The instructions may further cause the processor to control the social server to send the rescue request to a distress device server. The instructions may further cause the processor to control the distress device server to receive the rescue request sent by the social server, and instruct a rescue worker to travel to the geographical location identified in the rescue request to carry out rescue.

An eighth embodiment provides a computer storage medium storing processor-executable instructions that, when executed by a processor, cause the processor to receive a rescue request sent by a social server, where the rescue request is sent by a distress device in a vehicle when the vehicle is in a collision. The rescue request may include at least a geographical location of the vehicle and a device identifier of the distress device. The instructions may further cause the processor to instruct a rescue worker to travel to the geographical location identified in the rescue request to carry out rescue.

A ninth embodiment provides a computer storage medium storing processor-executable instructions that, when executed by a processor, cause the processor to receive a rescue request sent by a distress device in a vehicle when the vehicle is in a collision. The rescue request may include at least a geographical location of the vehicle and a device identifier. The instructions may further cause the processor to determine a social client associated with the device identifier, send the rescue request to the social client, and send the rescue request to a distress device server.

Beneficial effects such as improvements to the computer capabilities of the computing devices that provide the technical solutions provided in this application are at least as follows: When a vehicle has a collision, a distress device in the vehicle obtains a geographical location and a device identifier of the distress device, the distress device sends a rescue request to the social server, the social server determines, according to the received rescue request, a social client associated with the device identifier, and then sends the rescue request to the social client, the social server sends the rescue request to the distress device server, and the distress device server instructs, according to the received rescue request, a rescue worker to carry out rescue. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

BRIEF DESCRIPTION OF THE DRAWINGS

To describe the technical solutions of this application more clearly, the following briefly describes the accompanying drawings required for describing the embodiments. The accompanying drawings illustrates exemplary embodiments of the present disclosure, and a person of ordinary skill in the art may still derive other embodiments that are within the same scope from these accompanying drawings without creative efforts.

FIG. 1-2 shows a schematic diagram of an implementation environment for implementing another help seeking method according to some exemplary embodiments;

FIG. 2 shows a flowchart describing a help seeking method according to an exemplary embodiment;

DETAILED DESCRIPTION

To make the objectives, technical solutions, and advantages of this application clearer, the following further describes implementations of this application in detail with reference to the accompanying drawings.

Figure 1:
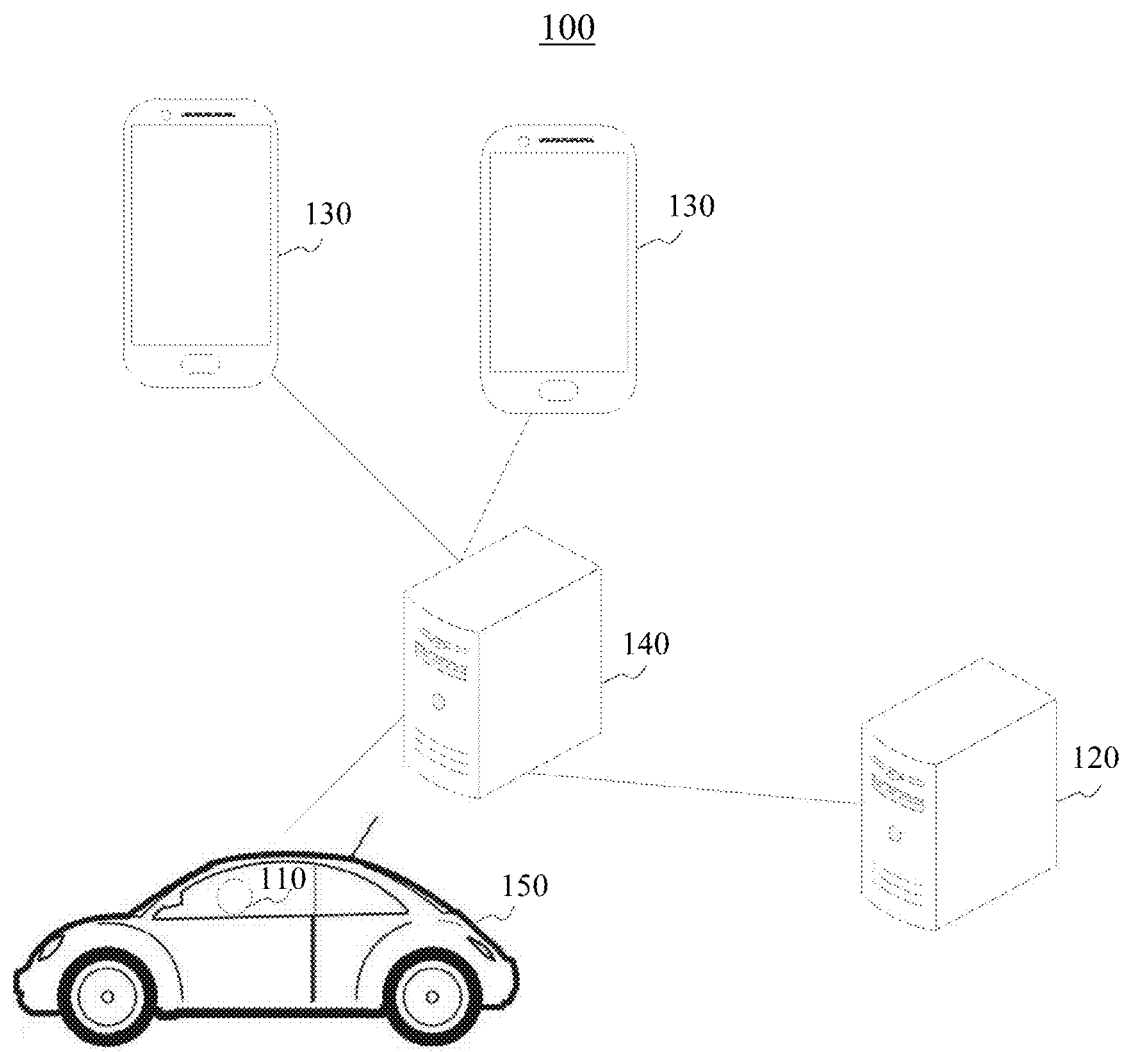
FIG. 1-1 shows a schematic diagram of an implementation environment for implementing a help seeking method according to some exemplary embodiments.

FIG. 1-1 is a schematic structural diagram of an implementation environment 100 according to this application. The implementation environment 100 includes a distress device 110, a distress device server 120, a terminal 130, and a social server 140.

The distress device 110 is installed in a vehicle 150, and has a data transmission capability. For example, the distress device may be an eCall device. The vehicle 150 is a transportation tool operating to enable a user to ride in the vehicle 150 instead of taking another mode of manual transportation such as, for example, walking, riding a bicycle, or taking a wheel chair.

The distress device server 120 is a background server of the distress device 110, and has a data transmission capability. Optionally, the distress device server 120 is monitored by a distress device service provider, and has a display function. When the distress device server 120 receives and displays a rescue request, the distress device service provider may instruct, according to the rescue request, a rescue worker to head for a place in which the vehicle has a collision, to carry out rescue.

The terminal 130 has a data transmission capability, and a social client is installed in the terminal 130. The social client is an instant messaging application, for example, MSN, Wechat, or QQ.

The social server 140 is a background server of the social client, and may be representative of a server cluster including one or more servers, or the social server 140 may be representative of a cloud computing center. The social server 140 stores a mapping relationship between a device identifier of a distress device and a social account that receives a rescue request when a vehicle has a collision.

The distress device 110 is connected to the social server 140 by means of a wireless network. The distress device server 120 is connected to the social server 140 by means of a wired network, a wireless network, or a data transmission line. The social client in at least one terminal 130 is connected to the social server 140 by means of a wired network, a wireless network, or a data transmission line.

Figures 1, 2:
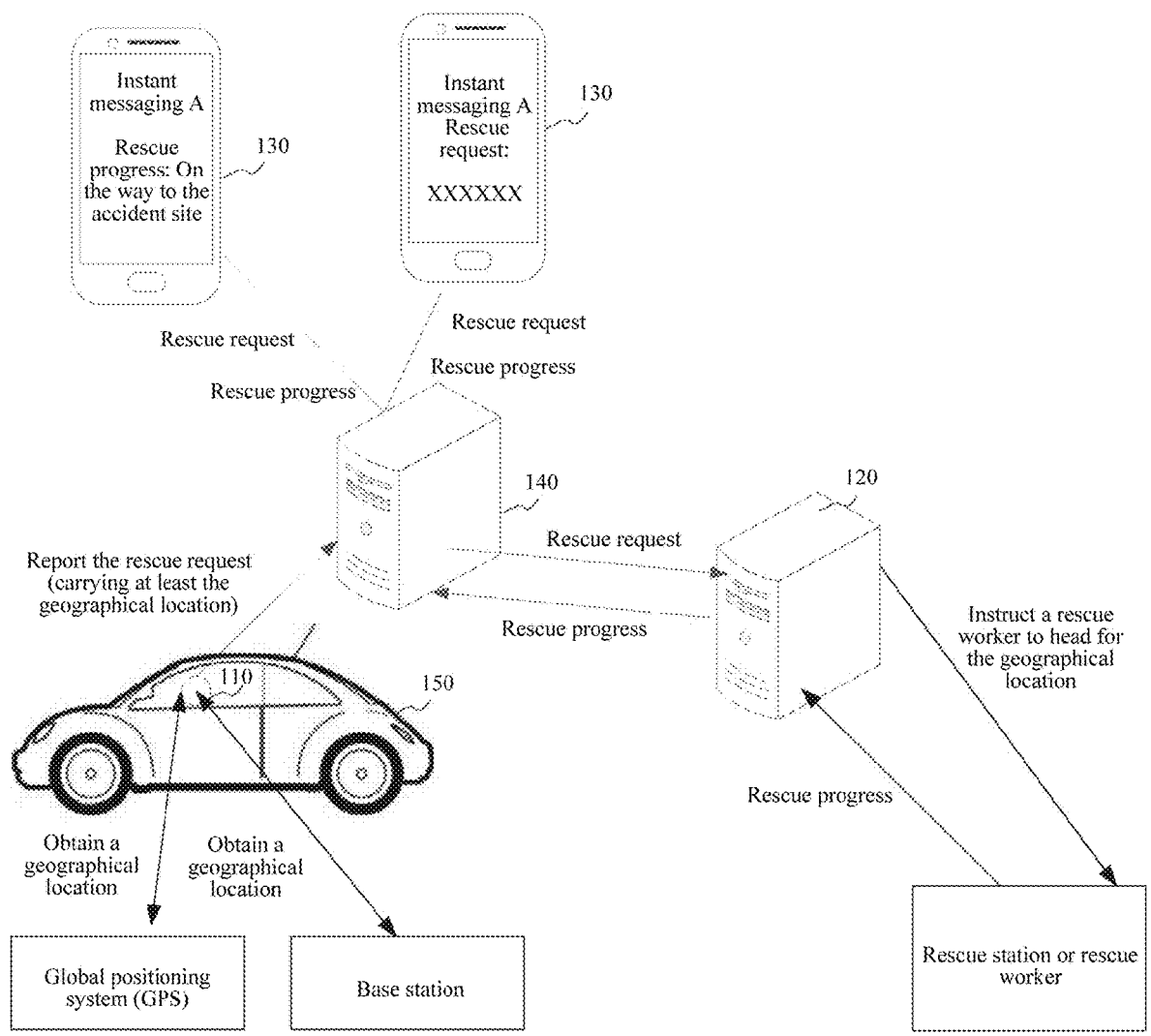
Figure 2:
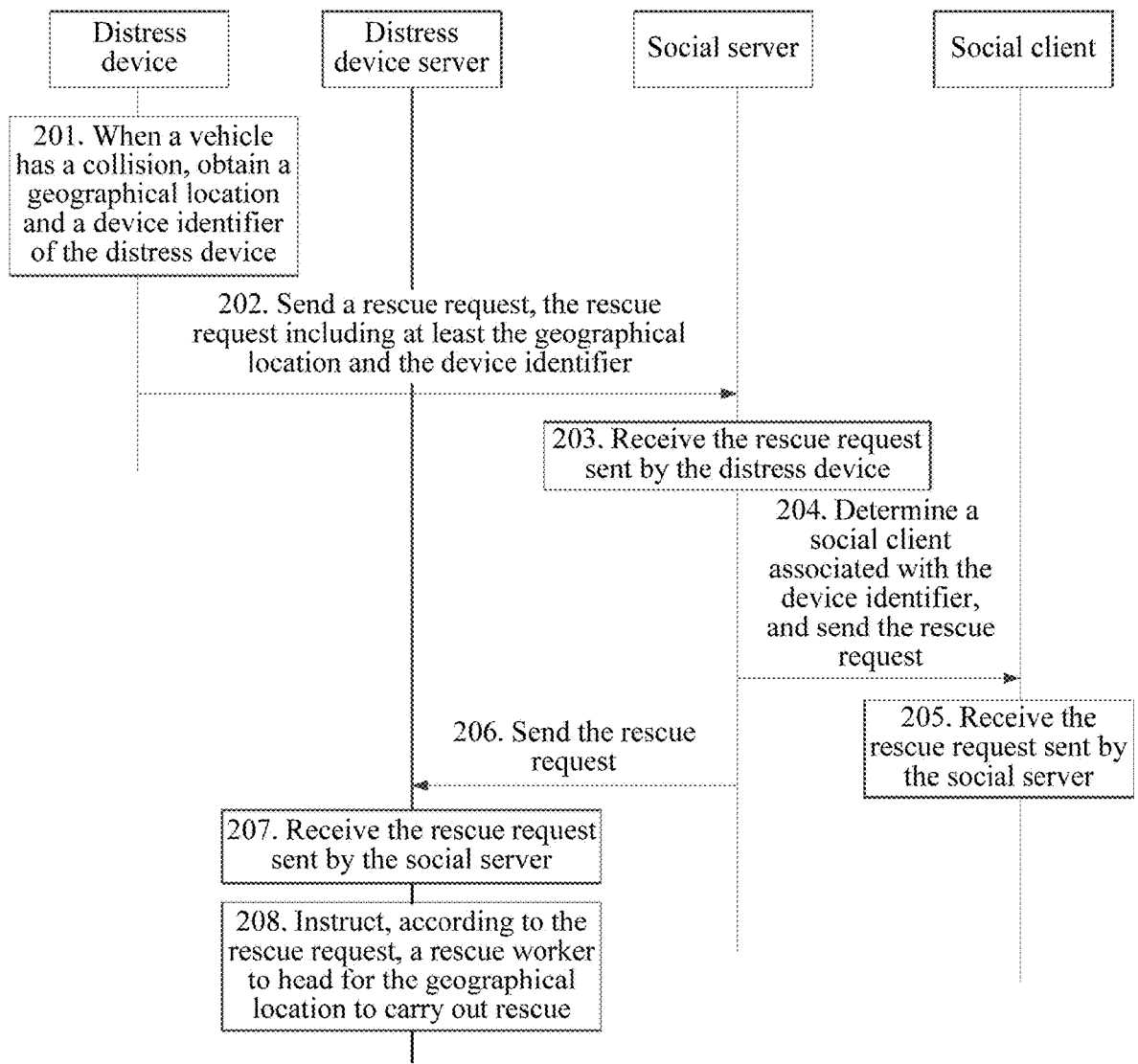

FIG. 2 shows a flowchart 200 of a help seeking method according to an exemplary embodiment of the present invention. This embodiment is described by using an example in which the help seeking method is applied to the implementation environment 100 shown in FIG. 1-1. The help seeking method includes the following steps.

Step 201. When a vehicle is detected to be involved in a collision, a distress device in the vehicle obtains a geographical location and a device identifier of the distress device.

When the vehicle has a collision, the distress device in the vehicle obtains the geographical location of a place in which the vehicle has a collision, and the device identifier of the distress device.

Step 202. The distress device sends a rescue request to a social server, the rescue request including at least the geographical location and the device identifier.

Step 203. The social server receives the rescue request sent by the distress device.

Step 204. The social server determines a social client associated with the device identifier, and sends the rescue request to the social client.

The social server determines, according to the device identifier carried in the received rescue request, the social client associated with the device identifier, and sends the rescue request to the determined social client.

Step 205. The social client receives the rescue request sent by the social server.

Step 206. The social server sends the rescue request to a distress device server.

Step 207. The distress device server receives the rescue request sent by the social server.

Step 208. The distress device server instructs, according to the rescue request, a rescue worker to head for the geographical location to carry out rescue.

It should be noted that the ordering of steps may be modified and still achieve the same result within the scope of the method illustrated in FIG. 2. For example, step 206 and step 207 may be performed before step 204 and step 205, or may be performed at the same time as step 204 and step 205. This is not limited in this embodiment.

Step 201 and step 202 may be independently implemented as an embodiment on the distress device side, step 203, step 204, and step 206 may be independently implemented as an embodiment on the social server side, and step 207 and step 208 may be independently implemented as an embodiment on the distress device server side.

Optionally, after receiving the rescue request sent by the social server, the distress device server instructs, according to the rescue request, the rescue worker to head for the geographical location of the place in which the vehicle has a collision, to carry out rescue.

It follows that in the help seeking method provided in this application, when a vehicle is involved in a collision, a distress device in the vehicle obtains a geographical location and a device identifier of the distress device, the distress device sends a rescue request to the social server, the social server determines, according to the received rescue request, a social client associated with the device identifier, and then sends the rescue request to the social client, the social server sends the rescue request to the distress device server, and the distress device server instructs, according to the received rescue request, a rescue worker to carry out rescue. Because when the vehicle is involved in a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

Figure 3:
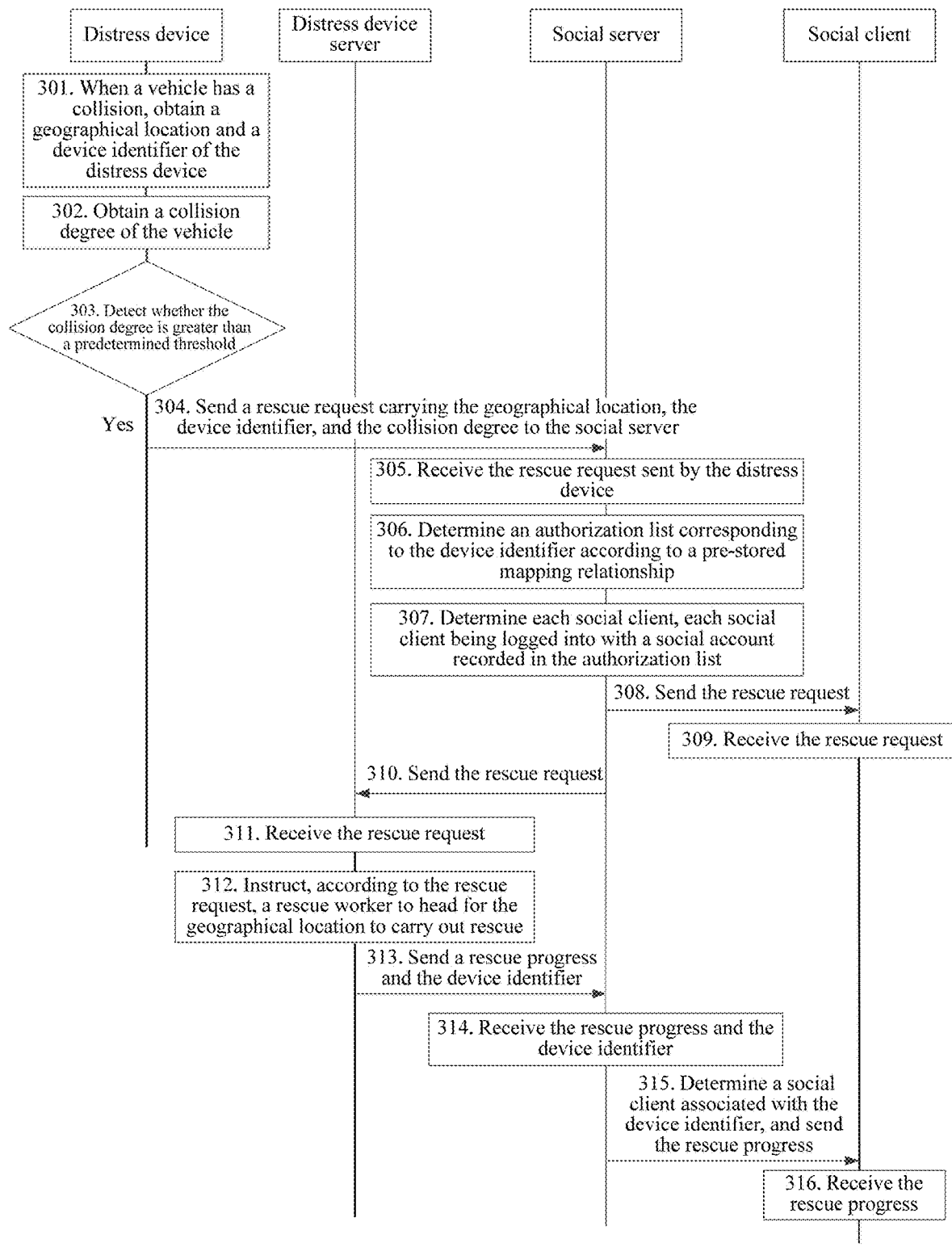
FIG. 3 shows a flowchart describing a help seeking method according to another exemplary embodiment.

FIG. 3 shows a flowchart 300 of a help seeking method according to another exemplary embodiment of the present invention. This embodiment is described by using an example in which the help seeking method is applied to the implementation environment 100 shown in FIG. 1-1. The help seeking method includes the following steps.

Step 301. When a vehicle has a collision, a distress device in the vehicle obtains a geographical location and a device identifier of the distress device.

A gravity-sensor (G-sensor) is installed in the distress device. The distress device may sense a change of accelerating force of the vehicle by means of the G-sensor, to determine, according to the change of the accelerating force, whether the vehicle is involved in a collision. The accelerating force is force physically imposed on an object during an accelerating process. When the object moves, for example, shakes, falls, rises, or descends, the movement can be converted into an electric signal by the G-sensor. When the vehicle has a collision during a driving process, the G-sensor converts the change of the accelerating force of the vehicle into the electric signal, and sends the electric signal to the distress device, and the distress device determines, according to the electric signal, whether the vehicle has a collision.

That is, when the vehicle has a collision or the like during the driving process, a communication signal is automatically sent to the distress device, so that the distress device learns that the vehicle has an accident.

When the distress device determines that the vehicle has a collision, the distress device obtains the geographical location of the place in which the vehicle has a collision, and the device identifier of the distress device. Specifically, the distress device may obtain the geographical location by means of a global positioning system (GPS), or a base station providing a data service, or the like. For example, referring to FIG. 1-2, when the vehicle has an accident, the distress device 110 is triggered. In this case, the distress device 110 obtains a current location of the vehicle by means of the GPS or the base station.

Step 302. The distress device obtains a collision degree of the vehicle.

According to some embodiments, the distress device may obtain the collision degree of the vehicle by means of the G-sensor. In a possible implementation, the distress device calculates a specific value of the collision degree by using the electric signal obtained through conversion by the G-sensor and the collision degree. In another possible implementation, the distress device determines a level of the collision degree according to the electric signal obtained through conversion by the G-sensor, for example, collision degrees corresponding to values of electric signals within a range correspond to a same level.

Step 303. The distress device detects whether the collision degree is greater than a predetermined threshold.

Because a vehicle owner may not be injured in the case of some collision degrees, and driving of the vehicle owner is not affected, to avoid resource wastes caused by the fact that the distress device frequently sends rescue requests to a social server, the distress device detects whether the collision degree is greater than the predetermined threshold, and when the collision degree is greater than the predetermined threshold, the distress device sends a rescue request to the social server, or if the collision degree is not greater than the predetermined threshold, the distress device does not sends a rescue request to the social server.

The predetermined threshold is preset by a user, or is a default value in the distress device. This is not limited in this embodiment. For example, the distress device sets a default predetermined threshold according to a model of the vehicle and an anti-collision capability of the vehicle.

Step 304. If the collision degree is greater than the predetermined threshold, the distress device sends a rescue request carrying the geographical location, the device identifier, and the collision degree to a social server.

Specifically, the rescue request sent by the distress device may be a sentence satisfying language logic, or may be several phrases that can represent the geographical location, the device identifier, and the collision degree. That is, after the distress device determines that the collision degree of the vehicle exceeds a threshold, the distress device automatically performs encapsulation based on the information such as the geographical location, the device identifier, and the collision degree, to obtain the rescue request.

For example, the geographical location of the place in which the vehicle has a collision is 31.5685 north latitude, 120.3841 east longitude, the device identifier is 2Q, and the collision degree is level 3. The rescue request sent by the distress device may be: The vehicle corresponding to the distress device 2Q has a level 3 collision in * building in * city, or 31.5685 north latitude, 120.3841 east longitude, 2Q, level 3.

If the collision degree is less than the predetermined threshold, the distress device does not send the rescue request to the social server. According to some embodiments, if the collision degree is less than the predetermined threshold, to feed back a collision status of the vehicle to a distress device server in time, the distress device may send the rescue request carrying the geographical location, the device identifier, and the collision degree to the distress device server, and after the distress device server receives the rescue request, a backend person of the distress device server determines whether to carry out subsequent rescue.

It should be noted that when the vehicle is involved in a collision, the distress device alternatively may not detect whether the collision degree is greater than the predetermined threshold, but directly obtains the geographical location and the device identifier of the distress device, and sends the rescue request carrying the geographical location and the device identifier to the social server. In this case, the distress device does not perform step 302 to step 304. The device identifier may be identifier information corresponding to the vehicle, for example, unique identification information such as a license plate number of the vehicle.

Step 305. The social server receives the rescue request sent by the distress device. For example, referring to FIG. 1-2, the distress device 110 reports the rescue request to the social server 140, and adds at least the geographical location to the rescue request.

Step 306. The social server determines an authorization list corresponding to the device identifier according to a pre-stored mapping relationship.

The mapping relationship is used to record a correspondence between a device identifier and an authorization list, and the authorization list is used record a social account that receives a rescue request when a vehicle has a collision. An authorization list corresponding to one device identifier records at least one social account. For example, the social account recorded in the authorization list may be social accounts of relatives and friends of the vehicle owner.

The following table exemplarily shows a part of the pre-stored mapping relationship in the social server.

| Device identifier | Social account |
| --- | --- |
| A1 | Xiaoming 1 |
|  | Xiaohua 2 |
| A2 | Xiaolv 1 |
| A3 | Xiaobai 1 |

According to some embodiments, the vehicle owner may associate the device identifier with the social account by means of the social client. For example, the vehicle owner adds the device identifier of the distress device to the social client, and sends, to a chosen social account, a request of associating the social account with the device identifier, and if the social account determines to be associated with the device identifier, the social server adds the social account to the authorization list corresponding to the device identifier. Alternatively, after the vehicle owner adds the device identifier of the distress device to the social client, the social server adds a social account whose contact frequency with a social account of the vehicle owner satisfies a condition to the authorization list, and this process may need to be acknowledged by the added social account, or may not need to be acknowledged by the added social account. Alternatively, after the vehicle owner adds the device identifier of the distress device to the social client, the social client adds social accounts in a particular group such as a friend and relative group to the authorization list, and this process may need to be acknowledged by the added social accounts, or may not need to be acknowledged by the added social accounts.

Step 307. The social server determines each social client, each social client being logged into with a social account recorded in the authorization list.

After determining the authorization list, the social server may obtain the social account in the authorization list, and determine the social client that is logged into with the social account in the authorization list.

Step 308. The social server sends the rescue request to the social client.

According to some embodiments, in order that a user of the social client conveniently reads rescue information, the rescue request sent by the social server to the social client may be a sentence satisfying language logic.

Step 309. The social client receives the rescue request sent by the social server. The social client is an instant messaging application, for example, MSN, Wechat, or QQ. For example, as shown in FIG. 1-2, the terminal 130 used as the social client receives the rescue request by means of instant messaging A.

Step 310. The social server sends the rescue request to the distress device server.

Step 311. The distress device server receives the rescue request sent by the social server.

It should be noted that the ordering of steps may be modified and still achieve the same result within the scope of the method illustrated in FIG. 3. For example, step 310 and step 311 may be performed before step 308 and step 309, or may be performed at the same time as step 308 and step 309.

Step 312. The distress device transmits instructions, according to the rescue request, for a rescue worker to head for the geographical location to carry out rescue. As shown in FIG. 1-2, the rescue request is sent to a rescue station or the rescue worker, so that the rescue station sends a rescue worker to the corresponding geographical location to carry out rescue. Alternatively, the rescue request is directly sent to the rescue worker, so that the rescue worker directly determines, according to the geographical location, a place needing rescue.

Step 313. The distress device server sends a rescue progress and the device identifier to the social server.

According to some embodiments, after receiving the rescue request, the distress device server instructs the rescue worker to head for the geographical location in which the collision occurs, to carry out rescue, or the backend person sends the rescue worker to the geographical location in which the collision occurs, to carry out rescue. The rescue worker feeds back the rescue progress and the device identifier to the distress device server, and the distress device server sends the rescue progress and the device identifier to the social server.

According to some embodiments, the rescue progress can represent a rescue status of the rescue worker for the vehicle collision event. For example, the rescue progress may include: On the way to the accident site, or approach the accident site, or already arrive at the accident site, or already send the vehicle owner to the hospital.

Step 314. The social server receives the rescue progress and the device identifier.

Step 315. The social server determines a social client associated with the device identifier, and sends the rescue progress to the social client.

A specific implementation in which the social server determines the social client associated with the device identifier is step 306 and step 307, and details are not described herein again.

The social server sends the rescue progress to the social client that is logged into with the social account in the authorization list, so that the user of the social client can learn the rescue progress in time. For example, as shown in FIG. 1-2, the left client may present the rescue progress of "On the way to the accident site".

According to some embodiments, the social server sends the rescue progress to all social clients that are logged into with social accounts in the authorization list, or the social server sends the rescue progress to some social clients that are logged into with social accounts in the authorization list.

Step 316. The social client receives the rescue progress sent by the social server.

Step 301 to step 304 may be independently implemented as an embodiment on the distress device side, step 305 to step 308, step 310, step 314, and step 315 may be independently implemented as an embodiment on the social server side, and step 311 to step 313 may be independently implemented as an embodiment on the distress device server side.

To sum up, in the help seeking method provided in this application, when a vehicle has a collision, a distress device in the vehicle obtains a geographical location and a device identifier of the distress device, the distress device sends a rescue request to the social server, the social server determines, according to the received rescue request, a social client associated with the device identifier, and then sends the rescue request to the social client, the social server sends the rescue request to the distress device server, and the distress device server instructs, according to the received rescue request, a rescue worker to carry out rescue. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

According to some embodiments based on the features shown in FIG. 2 or FIG. 3, a user may further actively query the rescue progress by means of the social client. That is, after step 311, the method further includes the following steps, as shown by the flowchart 400 in FIG. 4.

Step 401. The social client sends a rescue progress query request to the social server.

The rescue progress query request includes at least the device identifier and a login social account of the social client, and the social account is a social account recorded in the authorization list. Optionally, a user corresponding to the social account enters the device identifier and a rescue progress querying sentence in the social client, the social client generates the rescue progress query request according to the sentence entered by the user, and sends the rescue progress query request to the social server. Alternatively, a user triggers a shortcut key of querying the rescue progress in the social client, and the social client automatically generates the rescue progress query request according to the previously received device identifier, and sends the rescue progress query request to the social server.

For example, the social server has sent the rescue request carrying the device identifier Q2 to the social client, and the user enters "query the rescue progress, Q2" in the social client. Then, the social client automatically generates the rescue progress query request including at least the device identifier and the login social account of the social client, and sends the rescue progress query request to the social server. Alternatively, the user triggers the shortcut key of querying the rescue progress in the social client, and the social client generates, according to the device identifier Q2 previously received by the social client, the rescue progress query request including at least the device identifier and the login social account of the social client, and sends the rescue progress query request to the social server.

Step 402. The social server receives the rescue progress query request sent by the social client.

Step 403. The social server sends the rescue progress query request to the distress device server.

Step 404. The distress device server receives the rescue progress query request.

Step 405. The distress device server determines the rescue progress according to the device identifier carried in the rescue progress query request.

Optionally, the distress device server sends a rescue progress query to a rescue worker corresponding to the device identifier, and the rescue worker feeds back the rescue progress to the distress device server after receiving the rescue progress query. The rescue progress query may be directly sent to the rescue worker by the distress device server, or may be sent to the rescue worker by a backend person of the distress device server. Likewise, the rescue worker may directly feedback the rescue progress to the distress device server, or may feedback the rescue progress by means of the backend person of the distress device server.

Step 406. The distress device server sends the rescue progress and the device identifier to the social server.

Step 407. The social server receives the rescue progress and the device identifier.

Step 408. The social server determines the rescue progress query request according to the device identifier, and determines the social client according to the social account carried in the rescue progress query request.

Step 409. The social server sends the rescue progress to the social client.

Usually, the social server sends the rescue progress only to the social client corresponding to the social account sending the rescue progress query request. In a possible implementation, the social server may alternatively send the rescue progress to social clients corresponding to all social accounts in the authorization list corresponding to the device identifier. Correspondingly, the social client receives the rescue progress sent by the social server.

In addition, in the help seeking method provided in this application, the social client sends the rescue progress query request to the social server, and the social server feeds back the rescue progress only to the social client sending the rescue progress query request, so that the user can query the rescue progress in any time, and obtain related information of the rescue progress in time. The server feeds back the rescue progress only to a dedicated social client, so that the social server can process and send information more rapidly, and resources of the social server are saved.

Figure 4:
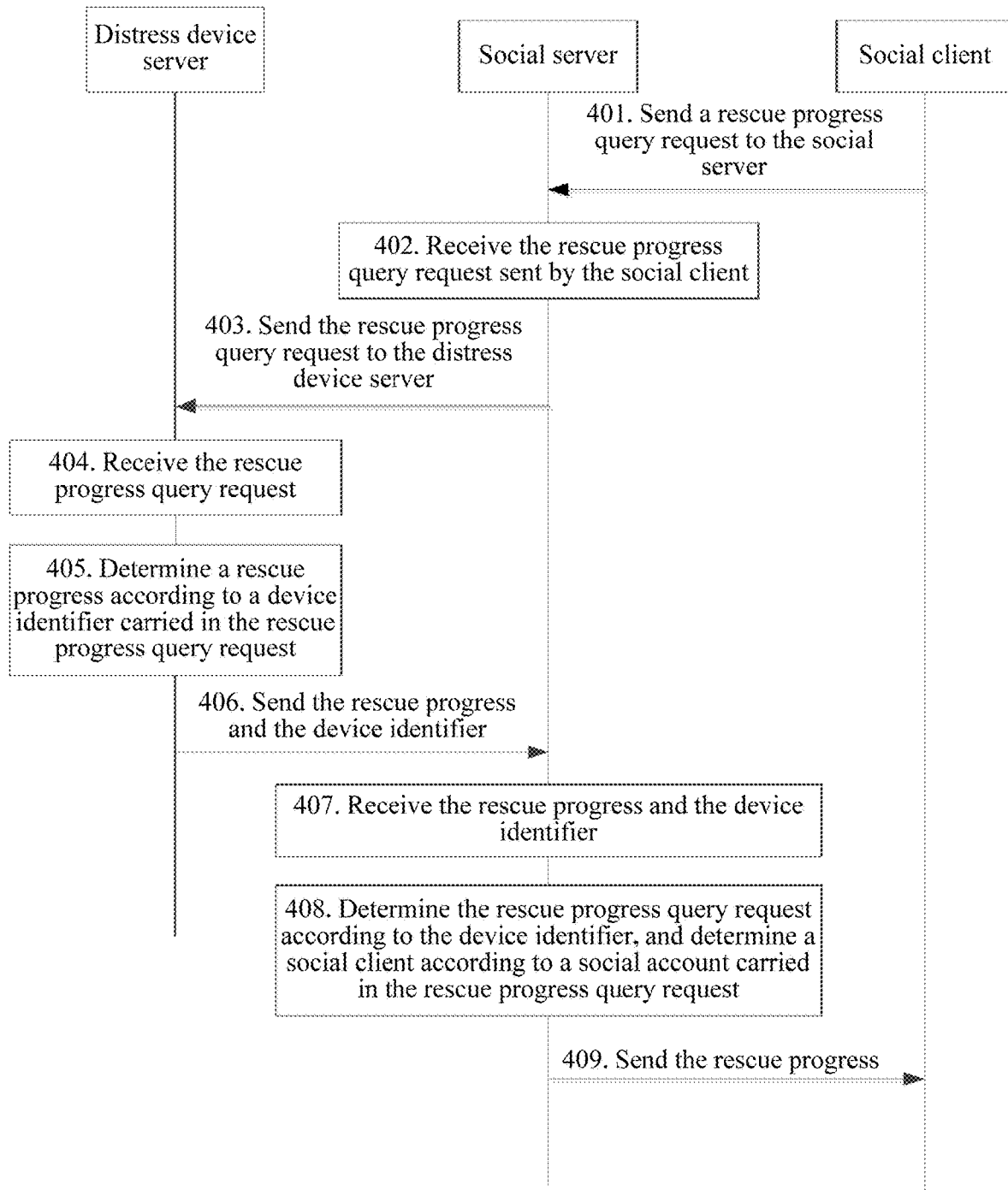
FIG. 4 shows a flowchart describing a help seeking method according to another exemplary embodiment.

It should be noted that, in the help seeking method provided in this application, only step 301 to step 311 in the embodiment shown in FIG. 3 and step 401 to step 409 in the embodiment shown in FIG. 4 may be performed. A person skilled in the art may further combine the steps according to an actual need, to obtain another implementation, and details are not described herein again.

Figure 5A:
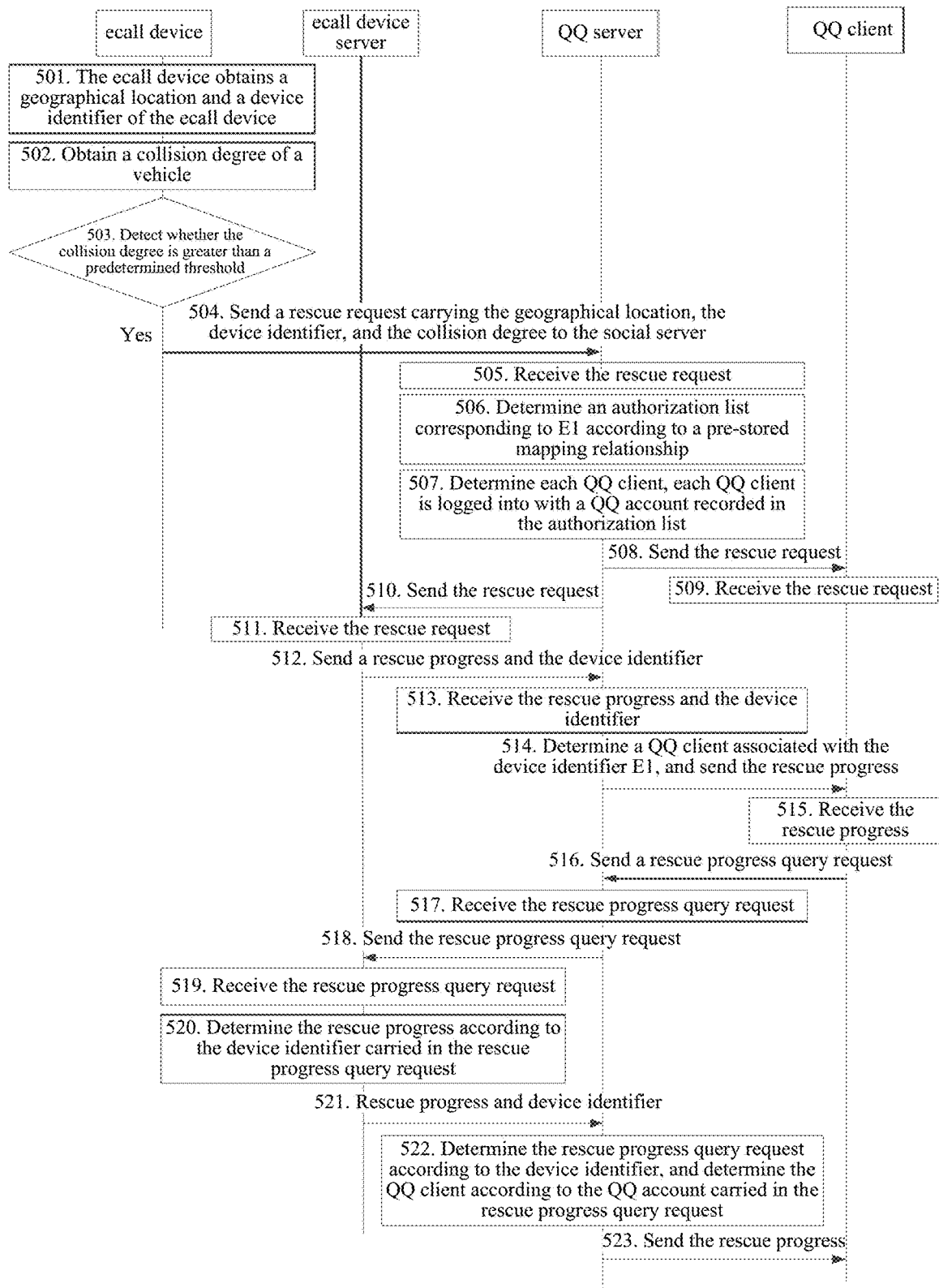
FIG. 5A shows a schematic diagram describing an implementation of a help seeking method according to an exemplary embodiment.

In an exemplary example, a vehicle having a collision is a car, a vehicle owner is Xiaowang, a distress device installed in the vehicle is an eCall device, a device identifier of the eCall device is E1, a social client is QQ, a social server is a QQ server, and a distress device server is an eCall server. As shown by the flowchart 500-A in FIG. 5A, the help seeking method includes the following steps.

Step 501. When the vehicle has a collision, the eCall device in the vehicle obtains a geographical location and the device identifier of the eCall device.

The eCall device determines, according to an electric signal sent by a G-sensor, that the vehicle has a collision, the geographical location that is obtained by means of the GPS and in which the collision occurs is 31.5685 north latitude, 120.3841 east longitude, and the obtained device identifier is E1.

Step 502. The eCall device obtains a collision degree of the vehicle.

The eCall device calculates according to the electric signal that the collision degree of the car is level 3.

Step 503. The eCall device detects whether the collision degree is greater than a predetermined threshold.

Assuming that the predetermined threshold is level 2, the eCall device detects that the collision degree of the car is greater than level 2.

Step 504. The eCall device sends a rescue request carrying the geographical location, the device identifier, and the collision degree to the QQ server.

The rescue request sent by the eCall device to the QQ server is: The car corresponding to the eCall device E1 has a level 3 collision event in 31.5685 north latitude, 120.3841 east longitude, please send the rescue immediately.

Step 505. The QQ server receives the rescue request sent by the eCall device.

Step 506. The QQ server determines an authorization list corresponding to E1 according to a pre-stored mapping relationship.

Three QQ accounts are recorded in the authorization list corresponding to E1 in the QQ server, namely, Xiaoli, Laowang, and Xiaohua.

Step 507. The QQ server determines each QQ client, each QQ client being logged into with a QQ account recorded in the authorization list.

The QQ server determines three QQ clients. The three QQ clients are respectively logged into with QQ accounts, Xiaoli, Laowang, and Xiaohua, and the three QQ accounts respectively correspond to the wife, the father, and the son of Xiaowang.

Step 508. The QQ server sends the rescue request to the QQ client.

The QQ server converts the geographical location into a specific location name according to the latitude and longitude of the geographical location in the received rescue request, and separately sends the rescue request to the QQ clients that are logged into with the QQ accounts of Xiaoli, Laowang, and Xiaohua Step 509. The QQ client receives the rescue request sent by the QQ server.

Figure 5B:
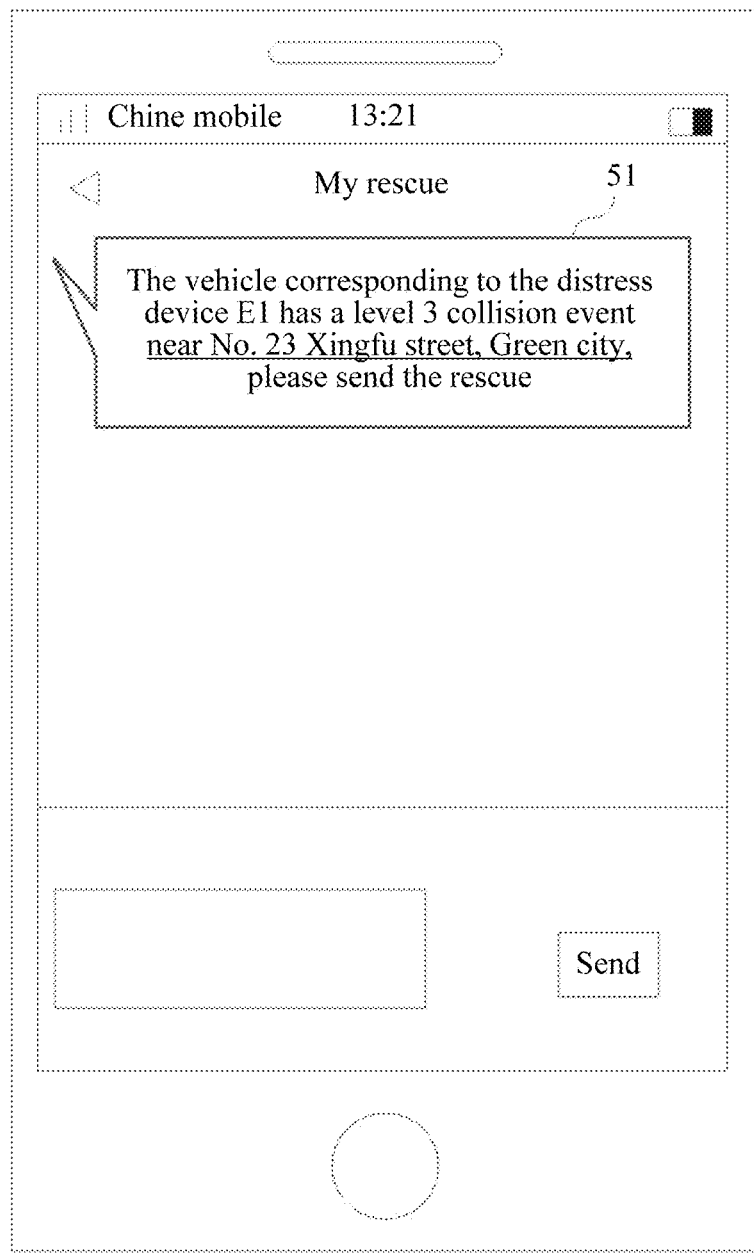
FIG. 5B shows a schematic diagram describing an implementation of a help seeking method according to an exemplary embodiment.

As shown by the graphical user interface (GUI) displayed by a smart device display screen in FIG. 5B, the QQ client of Xiaoli receives the rescue request sent by the QQ server, and the rescue request is "The vehicle corresponding to the distress device E1 has a level 3 collision event near No. 23

Xingfu street, Green city, please send the rescue" shown in 51. Likewise, the QQ clients of Laowang and Xiaoli receive the same rescue request.

Step 510. The QQ server sends the rescue request to the eCall device server.

Step 511. The eCall device server receives the rescue request sent by the QQ server.

After receiving the rescue request, the eCall device server sends the rescue worker to the place near No. 23 Xingfu street, Green city, to carry out rescue.

After the rescue worker arrives at the site, the rescue worker feeds back a rescue progress "Already arrive at the accident site" and the device identifier E1 to the eCall device server.

Step 512. The eCall device server sends a rescue progress and the device identifier to the QQ server.

The eCall device server sends the rescue progress "Already arrive at the accident site" and the device identifier E1 to the QQ server.

Step 513. The QQ server receives the rescue progress and the device identifier that are sent by the eCall device.

Step 514. The QQ server determines a QQ client associated with the device identifier E1, and sends the rescue progress to the QQ client.

The QQ server determines, according to the device identifier E1, that the QQ clients are QQ clients that are logged into with the QQ accounts of Xiaoli, Laowang, and Xiaohua, and sends the rescue progress to the three QQ clients.

Step 515. The QQ client receives the rescue progress sent by the QQ server.

Figure 5C:
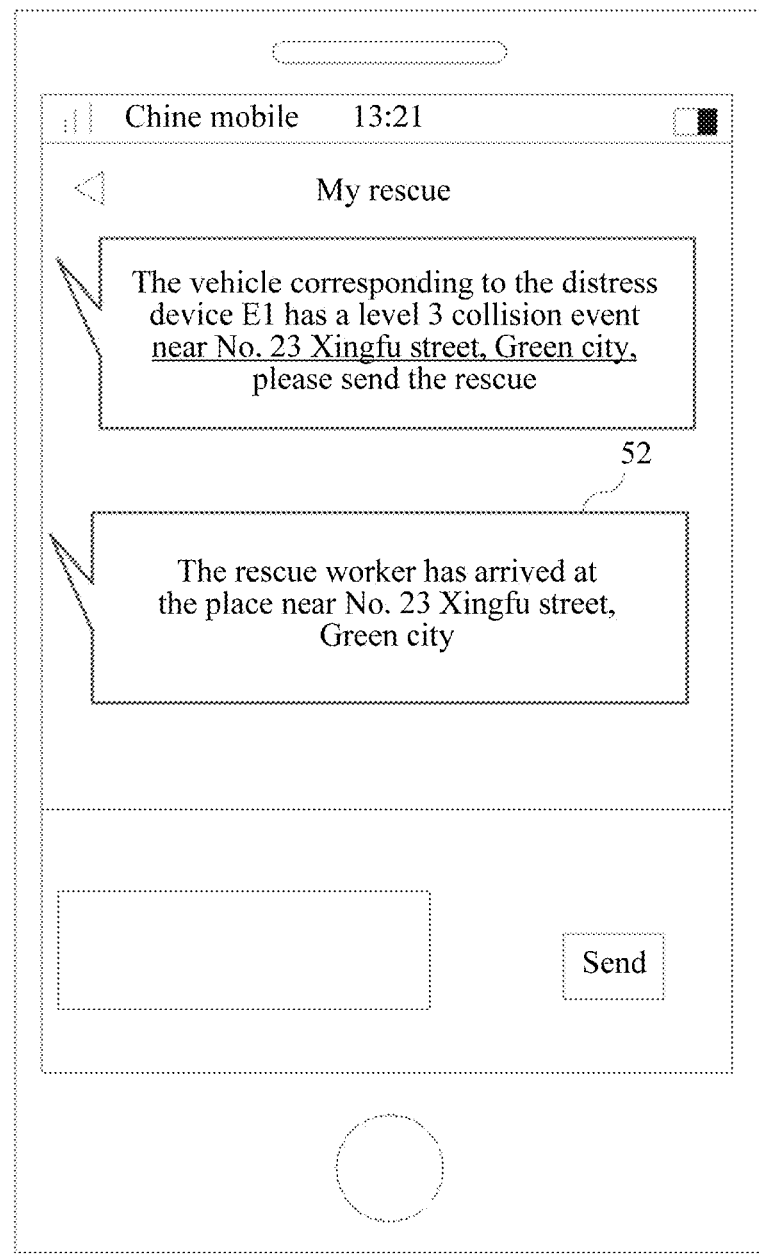
FIG. 5C shows a schematic diagram describing an implementation of a help seeking method according to an exemplary embodiment.

As shown by the graphical user interface (GUI) displayed by a smart device display screen in FIG. 5C, the QQ client of Xiaoli receives the rescue progress sent by the QQ server, and the rescue request may include a message stating "The rescue worker has arrived at the place near No. 23 Xingfu street, Green city" shown in 52. Likewise, the QQ clients of Laowang and Xiaohua receive the same rescue progress.

Step 516. The QQ client sends a rescue progress query request to the QQ server.

Figure 5D:
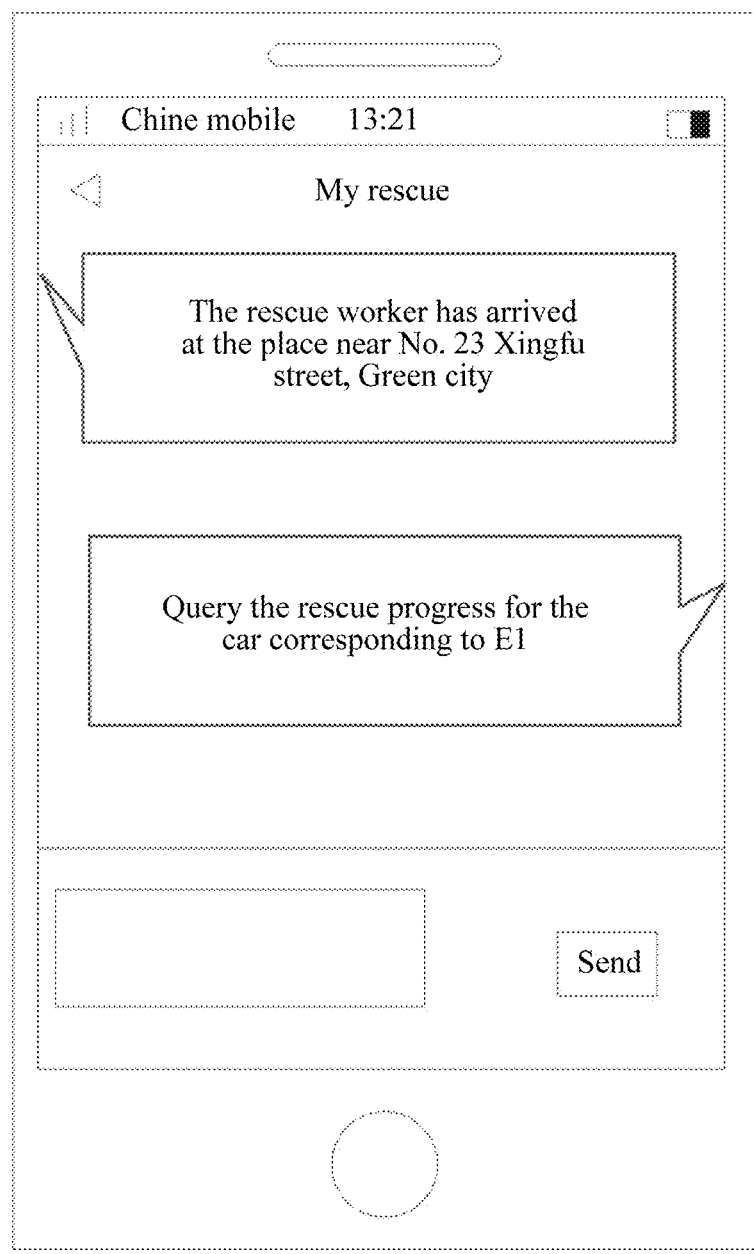
FIG. 5D shows a schematic diagram describing an implementation of a help seeking method according to an exemplary embodiment.

The QQ client that is logged into with the QQ account of Xiaohua sends the rescue progress query request "Query the rescue progress for the car corresponding to E1" to the QQ server, as shown by the graphical user interface (GUI) displayed by a smart device display screen in FIG. 5D.

The rescue progress query request further includes the login QQ account of Xiaohua of the QQ client.

Step 517. The QQ server receives the rescue progress query request sent by the QQ client.

Step 518. The QQ server sends the rescue progress query request to the eCall device server.

Step 519. The eCall device server receives the rescue progress query request sent by the server.

Step 520. The eCall device server determines the rescue progress according to the device identifier carried in the rescue progress query request.

The eCall device determines, according to the device identifier E1, that the rescue progress is "Already send the vehicle owner to the hospital".

Step 521. The eCall device server sends the rescue progress and the device identifier to the QQ server.

The eCall device sends the rescue progress "Already send the vehicle owner to the hospital" and the device identifier E1 to the QQ server.

Step 522. The QQ server determines the rescue progress query request according to the device identifier, and determines the QQ client according to the QQ account carried in the rescue progress query request.

The QQ server determines, according to the device identifier E1, that the rescue progress query request is from the QQ client that is logged into with the QQ account of Xiaohua.

Step 523. The QQ server sends the rescue progress to the QQ client.

The QQ server sends the rescue progress "Already send the vehicle owner to the hospital" to the QQ client that is logged into with the QQ account of Xiaohua.

Figure 5E:
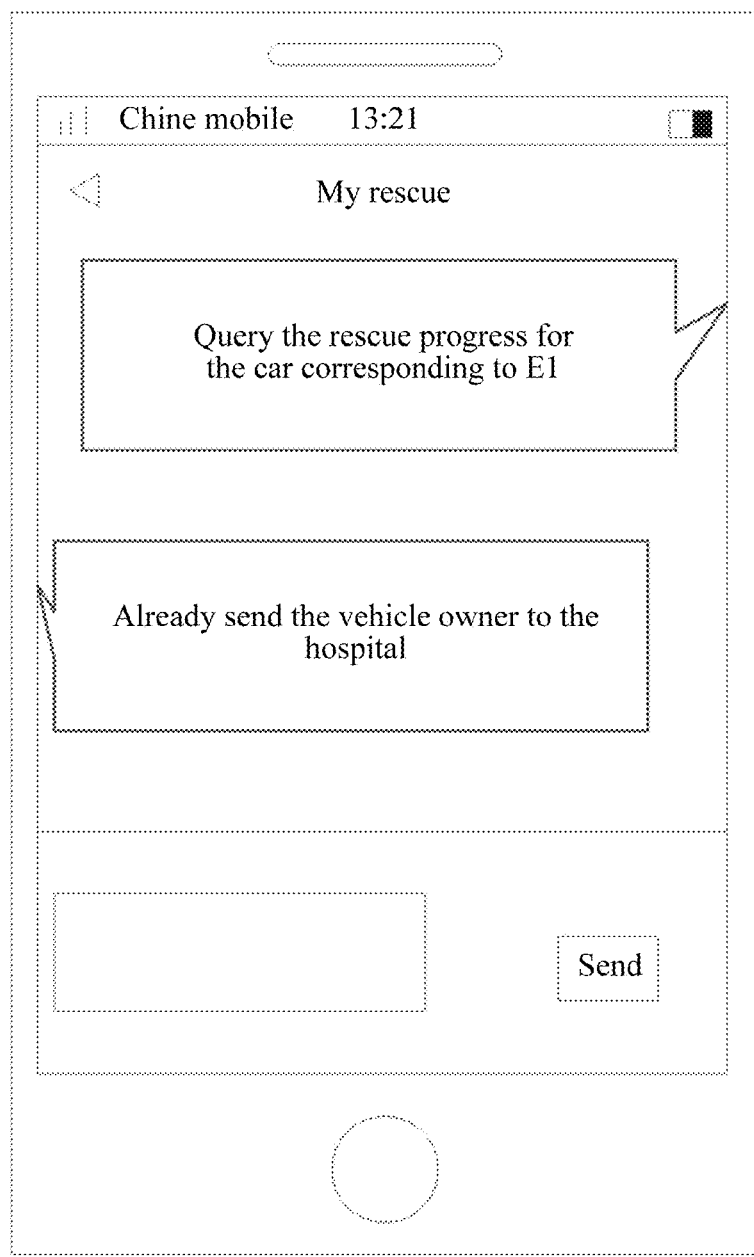
FIG. 5E shows a schematic diagram describing an implementation of a help seeking method according to an exemplary embodiment.

Correspondingly, the QQ client that is logged into with the QQ account of Xiaohua receives the rescue progress, as shown by the graphical user interface (GUI) displayed by a smart device display screen in FIG. 5E.

Figure 6:
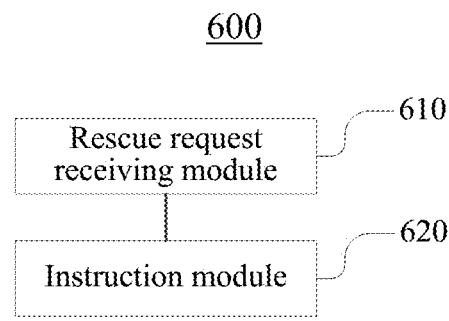
FIG. 6 shows a schematic block diagram of a help seeking apparatus according to an exemplary embodiment.

FIG. 6 shows a structural block diagram of a help seeking apparatus 600 according to an exemplary embodiment of the present invention. The help seeking apparatus 600 may be implemented as all or a part of the distress device server in the foregoing help seeking method by means of software, hardware, or a combination of software and hardware. The help seeking apparatus 600 includes a rescue request receiving module 610, configured to receive a rescue request sent by a social server, the rescue request being sent by a distress device in a vehicle to the social server when the vehicle has a collision, and the rescue request including at least a geographical location of the vehicle and a device identifier of the distress device. The help seeking apparatus 600 also includes an instruction module 620, configured to instruct, according to the rescue request received by the rescue request receiving module 610, a rescue worker to head for the geographical location to carry out rescue.

To sum up, in the help seeking apparatus provided in this application, when a vehicle has a collision, the distress device server receives the rescue request sent by the social server, and instructs the rescue worker to head for the geographical location to carry out rescue. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself, or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

Figure 7:
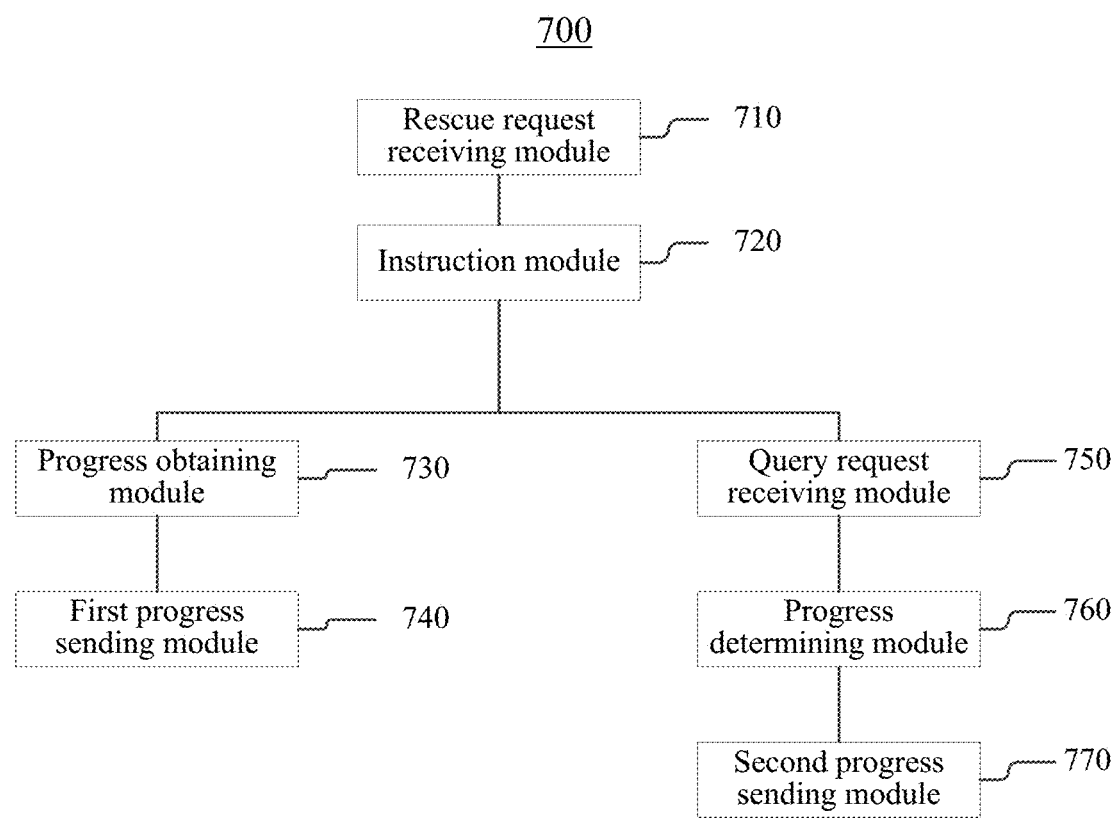
FIG. 7 shows a schematic block diagram of a help seeking apparatus according to another exemplary embodiment.

FIG. 7 is a structural block diagram of a help seeking apparatus 700 according to another exemplary embodiment of the present invention. The help seeking apparatus 700 may be implemented as all or a part of the distress device server in the foregoing help seeking method by means of software, hardware, or a combination of software and hardware. The help seeking apparatus 700 includes a rescue request receiving module 710, configured to receive a rescue request sent by a social server, the rescue request being sent by a distress device in a vehicle to the social server when the vehicle has a collision, and the rescue request including at least a geographical location of the vehicle and a device identifier of the distress device. The help seeking apparatus 700 also includes an instruction module 720, configured to instruct, according to the rescue request received by the rescue request receiving module 710, a rescue worker to head for the geographical location to carry out rescue.

According to some embodiments, the help seeking apparatus 700 may further include a progress obtaining module 730, configured to obtain a rescue progress of the rescue worker for the vehicle, and a first progress sending module

740, configured to send the rescue progress obtained by the progress obtaining module 730 and the device identifier to the social server.

According to some embodiments, the help seeking apparatus 700 may further include a query request receiving module 750, configured to receive a rescue progress query request sent by the social server, where the rescue progress query request is sent by a social client to the social server, the rescue progress query request includes at least the device identifier and a login social account of the social client, the social client is logged into with a social account in an authorization list, and the authorization list is used to record a social account that receives a rescue request when a vehicle has a collision, a progress determining module 760, configured to determine the rescue progress according to the device identifier carried in the rescue progress query request received by the query request receiving module 750, and a second progress sending module 770, configured to send the rescue progress determined by the progress determining module 760 and the device identifier to the social server.

To sum up, in the help seeking apparatus provided in this application, when a vehicle has a collision, the distress device server receives the rescue request sent by the social server, and instructs the rescue worker to head for the geographical location to carry out rescue. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself, or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

Figure 8:
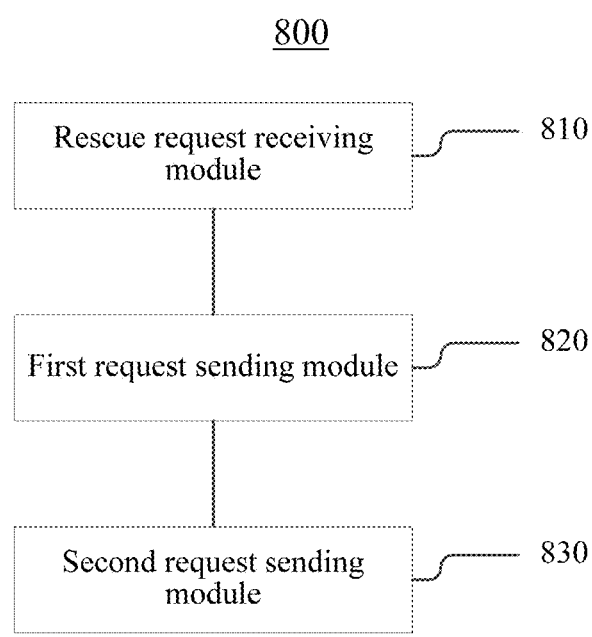
FIG. 8 shows a schematic block diagram of a help seeking apparatus according to an exemplary embodiment.

FIG. 8 is a structural block diagram of a help seeking apparatus 800 according to an embodiment of the present invention. The help seeking apparatus 800 may be implemented as all or a part of the social server in the foregoing help seeking method by means of software, hardware, or a combination of software and hardware. The help seeking apparatus 800 includes a rescue request receiving module 810, configured to receive a rescue request that is sent by a distress device in a vehicle when the vehicle has a collision, the rescue request including at least a geographical location of the vehicle and a device identifier, a first request sending module 820, configured to determine a social client associated with the device identifier, and send the rescue request to the social client, and a second request sending module 830, configured to send the rescue request to a distress device server.

To sum up, in the help seeking apparatus provided in this application, when a vehicle has a collision, the social server receives the rescue request sent by the distress device, and the social server determines the social client associated with the device identifier, and sends the rescue request to the social client and the distress device server. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself, or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

Figure 9:
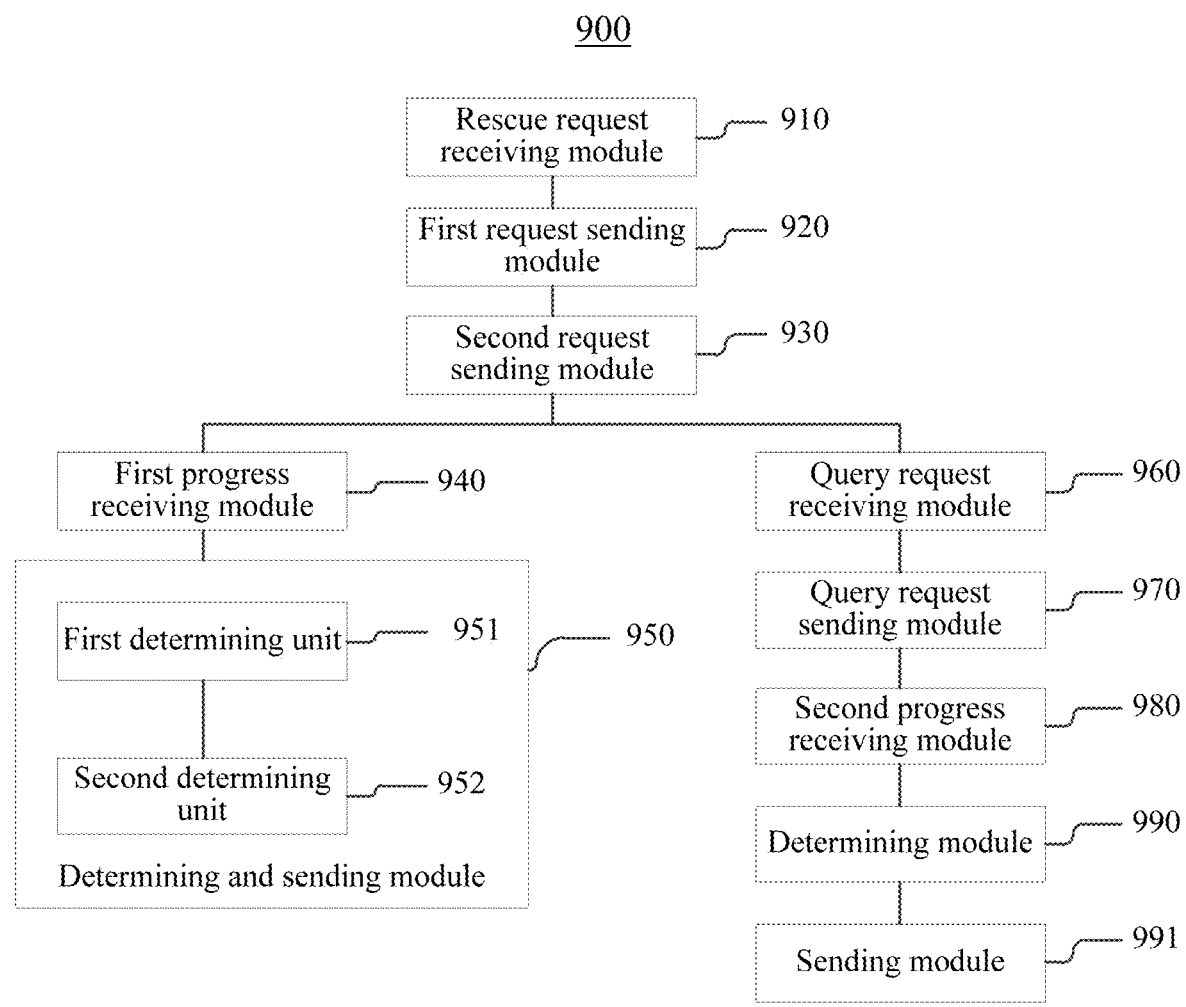
FIG. 9 shows a schematic block diagram of a help seeking apparatus according to an exemplary embodiment.

FIG. 9 is a structural block diagram of a help seeking apparatus 900 according to another embodiment of the present invention. The help seeking apparatus 900 may be implemented as all or a part of the social server in the foregoing help seeking method by means of software, hardware, or a combination of software and hardware. The help seeking apparatus 900 includes a rescue request receiving module 910, configured to receive a rescue request that is sent by a distress device in a vehicle when the vehicle has a collision, the rescue request including at least a geographical location of the vehicle and a device identifier, a first request sending module 920, configured to determine a social client associated with the device identifier, and send the rescue request to the social client, and a second request sending module 930, configured to send the rescue request to a distress device server.

According to some embodiments, the help seeking apparatus 900 further includes a first progress receiving module 940, configured to receive a rescue progress and the device identifier that are sent by the distress device server, and a determining and sending module 950, configured to determine the social client associated with the device identifier, and send the rescue progress to the social client.

According to some embodiments, the determining and sending module 950 includes: a first determining unit 951, configured to determine an authorization list corresponding to the device identifier according to a pre-stored mapping relationship, where the mapping relationship is used to record a correspondence between a device identifier and an authorization list, and the authorization list is used to record a social account that receives a rescue request when a vehicle has a collision, and a second determining unit 952, configured to determine each social client, where each social client is logged into with a social account recorded in the authorization list.

According to some embodiments, the help seeking apparatus 900 further includes a query request receiving module 960, configured to receive a rescue progress query request sent by the social client, where the rescue progress query request includes at least the device identifier and a login social account of the social client, and the social account is a social account recorded in the authorization list, a query request sending module 970, configured to send the rescue progress query request to the distress device server, a second progress receiving module 980, configured to receive the rescue progress and the device identifier that are sent by the distress device server, where the rescue progress is determined and sent by the distress device server according to the device identifier, a determining module 990, configured to determine the rescue progress query request according to the device identifier, and determine the social client according to the social account carried in the rescue progress query request, and a sending module 991, configured to send the rescue progress to the social client.

To sum up, in the help seeking apparatus provided in this application, when a vehicle has a collision, the social server receives the rescue request sent by the distress device, and the social server determines the social client associated with the device identifier, and sends the rescue request to the social client and the distress device server. Because when the vehicle has a collision, the distress device sends the rescue request to the social server, and the social server sends the rescue request to the social client and the distress device server, and a vehicle owner does not need to seek help by using the distress device, a problem that the best rescue time is easily missed because the vehicle owner cannot seek help by himself or herself, or other rescue workers cannot arrive in time is avoided, relatives and friends of the vehicle owner can be notified in time, the relatives and friends can pay close attention to the vehicle owner, the rescue efficiency can be improved, and deaths and injuries can be reduced.

It should be noted that when implementing the help seeking method, the help seeking apparatuses provided in the embodiments are merely described by using division of functional modules as an example. In an actual application, the foregoing functions may be allocated to different functional modules for completion according to requirements. That is, the internal structure of the device is divided into different functional modules, to complete all or a part of functions described above. In addition, the help seeking apparatuses provided in the foregoing embodiments and the embodiment of the help seeking method belong to a same concept. For a specific implementation process, refer to the method embodiment, and details are not described herein again.

The sequences numbers of this application are merely used for description, but do not represent preferences of the embodiments.

A person of ordinary skill in the art may understand that all or some of the steps of the foregoing embodiments may be implemented by using hardware, or may be implemented by a program instructing relevant hardware. The program may be stored in a computer readable storage medium. The storage medium may be a read-only memory, a magnetic disk, an optical disc, or the like.

The foregoing descriptions are merely preferred embodiments of the present invention, but are not intended to limit the present disclosure. Any modification, equivalent replacement, or improvement made within the spirit and principle of the present disclosure shall fall within the protection scope of the present disclosure.

Figure 10:
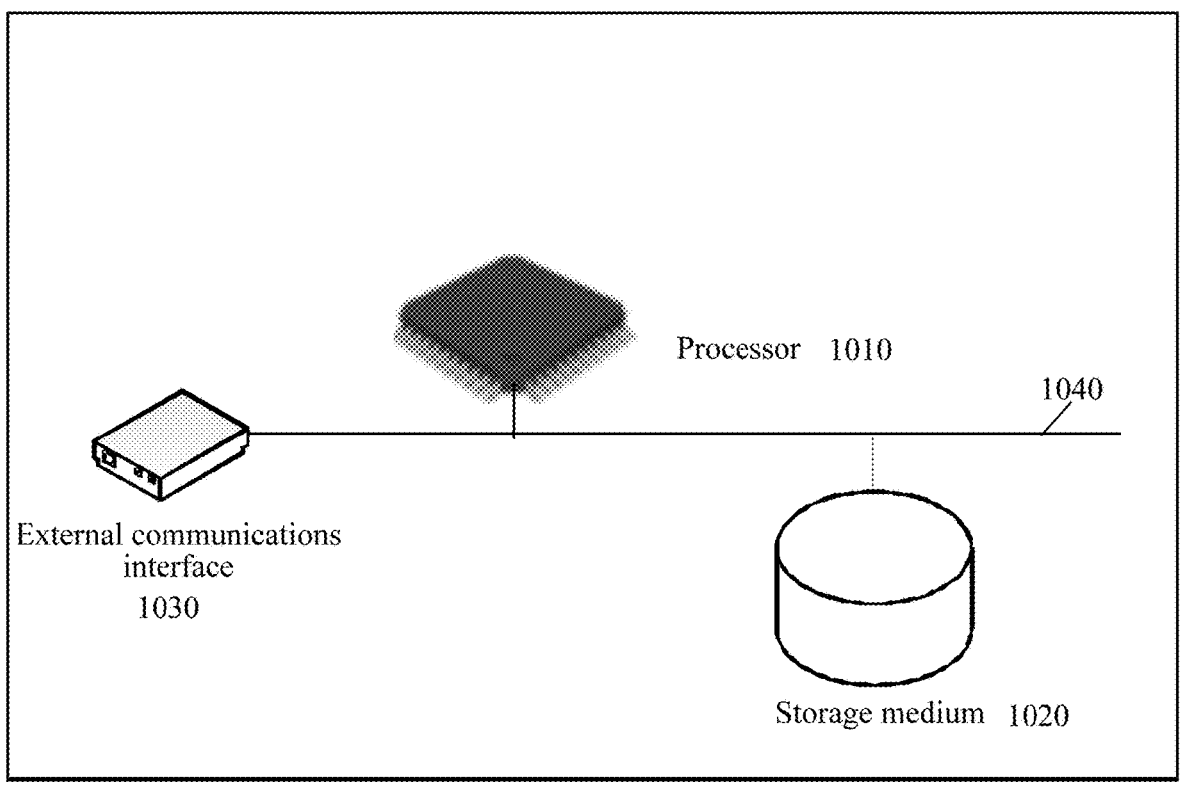
FIG. 10 shows a schematic structural diagram of hardware composition according to this application.

Based on the foregoing scenario, an example in which the apparatus 1000 provided in the embodiments is used as a hardware entity is shown in FIG. 10. The apparatus 1000 includes a processor 1010, a storage medium 1020, and at least one external communications interface 1030. The processor 1010, the storage medium 1020, and the external communications interface 1030 are connected by using a bus 1040.

The processor of the apparatus 1000 in this application performs the following processing:

when a vehicle has a collision, obtaining, by a distress device in the vehicle, a geographical location and a device identifier of the distress device;

sending, by the distress device, a rescue request to a social server, the rescue request including at least the geographical location and the device identifier;

receiving, by the social server, the rescue request sent by the distress device;

determining, by the social server, a social client associated with the device identifier, and sending the rescue request to the social client;

receiving, by the social client, the rescue request sent by the social server;

sending, by the social server, the rescue request to a distress device server;

receiving, by the distress device server, the rescue request sent by the social server; and instructing, by the distress device server according to the rescue request, a rescue worker to head for the geographical location to carry out rescue.

According to some embodiments, the processor 1010 of the apparatus in this application performs the following processing:

receiving a rescue request sent by the social server, the rescue request being sent by a distress device in a vehicle to the social server when the vehicle has a collision, and the rescue request including at least a geographical location of the vehicle and a device identifier of the distress device; and instructing, according to the rescue request, a rescue worker to head for the geographical location to carry out rescue.

According to some embodiments, the processor 1010 of the apparatus in this application performs the following processing:

receiving a rescue request that is sent by a distress device in a vehicle when the vehicle has a collision, the rescue request including at least a geographical location of the vehicle and a device identifier; and determining a social client associated with the device identifier, sending the rescue request to the social client, and sending the rescue request to a distress device server.

A person of ordinary skill in the art may understand that all or a part of processes in the method in the foregoing embodiment may be implemented by a computer program instructing relevant hardware. The program may be stored in a computer readable storage medium. For example, in this application, the program may be stored in a storage medium of a computer system, and is performed by at least one processor of the computer system, to implement processes of the embodiment of the foregoing method. The storage medium may be a magnetic disk, an optical disc, a read-only memory (ROM), a random access memory (RAM), or the like.

Technical features of the foregoing embodiments may be combined in any manner. For brevity of descriptions, not all possible combinations of the technical features in the foregoing embodiments are described. Provided that no contradiction exists between the combinations of these technical features, it should be considered that the combinations should fall within the scope of this specification.

The foregoing embodiment merely describes some implementations of the present disclosure, and the descriptions are specific and detailed, but cannot be understood as a limitation to the patent scope of the present disclosure. It should be noted that a person of ordinary skill in the art may make various variations and improvements without departing from the concept of the present disclosure, and theses shall belong to the protection scope of the present disclosure. Therefore, the protection scope of the present disclosure shall be subjected to the appended claims.

What is claimed is:

1. A help seeking method, implemented by a help seeking system comprising a distress device, a distress device server, a social server, and a social client account, the social server being separately connected to the distress device and the distress device server, and the social server being a background server of the social client, and the method comprising:

determining, by the distress device included in a vehicle, the vehicle is involved in a collision, and obtaining a geographical location of the distress device and a device identifier of the distress device;

sending, by the distress device, a rescue request to the social server, the rescue request comprising at least the geographical location and the device identifier;

receiving, by the social server, the rescue request sent by the distress device;

determining, by the social server, a social client account associated with the device identifier, wherein the social client account is hosted by the social server;

including, by the social server, the rescue request with the social client account, wherein information included in the rescue request is displayable on a computing device accessing the social client account;

displaying, on a graphical user interface associated with the social client account, the rescue request, wherein the graphical user interface associated with the social client account is configured to be viewable by other social client accounts of the social server that are included in an authorization list corresponding with the social client account;

sending, by the social server, the rescue request to the distress device server;

receiving, by the distress device server, the rescue request sent by the social server; and generating, by the distress device server according to the rescue request, a message including the geographical location for a rescue worker;

generating, by the distress device server, a rescue progress message in response to one or more rescue progress query requests sent by a subset of one or social client accounts of the other social client accounts, wherein a number of the subset is less than a total number of the other social client accounts;

sending, by the distress device server, the rescue progress message to the social server;

receiving, by the social server, the rescue progress message; and sending, by the social server, the rescue progress message only to the subset of the other social client accounts of the social server that are included in the authorization list corresponding with the social client account and that sent the one or more rescue progress query requests.

2. The method according to claim 1, wherein the determining, by the social server, the social client account associated with the device identifier comprises:

determining, by the social server, the authorization list corresponding to the device identifier according to a pre-stored mapping relationship; and determining, by the social server for each social client account, each of the other social client accounts included in the authorization list that are logged into.

3. The method according to claim 1, wherein when the rescue request further comprises a collision degree of the vehicle, sending the rescue request to the social server comprises:

obtaining, by the distress device, a collision degree of the vehicle;

detecting, by the distress device, the collision degree is greater than a predetermined threshold; and sending, by the distress device, the rescue request carrying the geographical location, the device identifier, and the collision degree to the social server.

4. The method according to claim 1, wherein the distress device server is a background server of the distress device.

5. A help seeking system comprising:

a distress device included in a vehicle, the distress device configured to:

when a vehicle is detected to be in a collision, obtain a geographical location and a device identifier of the distress device; and send a rescue request to a social server, the rescue request comprising at least the geographical location and the device identifier;

the social server configured to:

receive the rescue request sent by the distress device;

determine a social client account associated with the device identifier, and send the rescue request to the social client account, wherein the social client account is hosted by the social server;

include the rescue request with the social client account, wherein information included in the rescue request is displayable on a computing device accessing the social client account;

display, on a graphical user interface associated with the social client account, the rescue request, wherein the graphical user interface associated with the social client account is configured to be viewable by other social client accounts of the social server that are included in an authorization list corresponding with the social client account;

send the rescue request to a distress device server; and a distress device server configured to:

receive the rescue request sent by the social server;

generate, according to the rescue request, a message including the geographical location for a rescue worker;

generate a rescue progress message in response to one or more rescue progress query requests sent by a subset of one or more social client accounts of the other social client accounts, wherein a number of the subset is less than a total number of the other social client accounts; and send the rescue progress message to the social server;

wherein the social server is further configured to:

receive the rescue progress message; and send the rescue progress message only to the subset of the other social client accounts of the social server that are included in the authorization list corresponding with the social client account and that sent the one or more rescue progress query requests.

6. The system according to claim 5, wherein:

a computing device corresponding to the social server is configured to:

determine the authorization list corresponding to the device identifier according to a pre-stored mapping relationship; and determine each social client account, each of the other social client accounts included in the authorization list that are logged into.

7. The system according to claim 5, wherein the distress device is further configured to:

obtain a collision degree of the vehicle;

detect the collision degree is greater than a predetermined threshold; and send the rescue request including the geographical location, the device identifier, and the collision degree to the social server.

8. The system according to claim 7, wherein the distress device includes a gravity sensor configured to obtain the collision degree of the vehicle.

9. The system according to claim 5, wherein the distress device is configured to obtain the geographical location of the distress device by communicating with a global positioning system.

10. The system according to claim 5, wherein the distress device server is a background server of the distress device.

11. A distress device server in communication with a social server, the distress device server comprising:

a processor; and a memory storing processor-executable instructions that, when executed by the processor, cause the processor to:

receive a rescue request sent by the social server, wherein the rescue request is transmitted to the social server by a distress device included in a vehicle when the vehicle is detected to be involved in a collision, wherein the rescue request includes at least a geographical location of the vehicle and a device identifier of the distress device, and wherein the distress device is also configured to provide the rescue request to a social client account, and wherein the social server is configured to display the rescue request on a graphical user interface associated with the social client account, wherein the graphical user interface associated with the social client account is configured to be viewable by other social client accounts of the social server that are included in an authorization list corresponding with the social client account; and generate, according to the rescue request, a message including the geographical location for a rescue worker;

instruct, according to the rescue request, a rescue worker to travel to the geographical location to carry out rescue;

generate a rescue progress message in response to one or more rescue progress query requests sent by a subset of one or more social client accounts of the other social client accounts, wherein a number of the subset is less than a total number of the other social client accounts; and send the rescue progress message to the social server, wherein the social server is configured to receive the rescue progress message, and send the rescue progress message only to the subset of the other social client accounts of the social server that are included in the authorization list corresponding with the social client account and that sent the one or more rescue progress query requests.

12. The distress device server according to claim 11, wherein the social client account is logged into with a social account in the authorization list, and the authorization list is used to record a social account that receives a rescue request when the vehicle is detected to be involved in the collision.

13. The distress device server according to claim 11, wherein the distress device server is a background server of the distress device.

14. The distress device server according to claim 11, wherein the processor-executable instructions, when executed by the processor, causes the processor to receive the rescue request from the social server when a collision degree detected by the distress device is greater than a predetermined threshold.

* * * * *